United States Patent [19]

Hunter et al.

[11] Patent Number: 4,707,447

[45] Date of Patent: * Nov. 17, 1987

[54] FUNGAL CHLOROPEROXIDASE METHOD

[75] Inventors: Jennie C. Hunter, El Cerrito; Angela Belt; Lynn S. Sotos, both of Oakland; Michelle E. Fonda, Albany, all of Calif.

[73] Assignee: Cetus Corporation, Emeryville, Calif.

[*] Notice: The portion of the term of this patent subsequent to Nov. 17, 2004 has been disclaimed.

[21] Appl. No.: 497,658

[22] Filed: May 24, 1983

[51] Int. Cl.[4] .......................... C12P 7/00; C12P 9/00; C12P 7/16; C12N 9/08

[52] U.S. Cl. ................................. 435/132; 435/131; 435/156; 435/157; 435/158; 435/160; 435/188; 435/189; 435/192

[58] Field of Search ............... 435/157, 158, 183, 188, 435/189, 192, 211, 131, 132, 156

[56] References Cited

U.S. PATENT DOCUMENTS

| | | | |
|---|---|---|---|
| 4,246,347 | 1/1981 | Neidleman et al. | 435/105 |
| 4,247,641 | 1/1981 | Neidleman et al. | 435/123 |
| 4,284,723 | 8/1981 | Neidleman et al. | 435/123 |
| 4,379,141 | 4/1983 | Hasegawa et al. | 424/94 |

FOREIGN PATENT DOCUMENTS

0099192  6/1982  Japan ................................. 435/192

OTHER PUBLICATIONS

"Chloroperoxidase" by John Thomas in: J. of Biol. Chem., 245(12) 3135-3142, Jun. 25, 1970.
Ichikawa, K. et al–Chem. Abstracts, vol. 95, #37873z, 1981, "Partial Purification and Characterization of Peroxidase".
Singh, P.N.–Chem. Abstracts, vol. 87, #98645h, 1977, "Nutrition of Alternaria Alternata".
Kozhanova et al–Chem. Abstracts, vol. 86, #13956s, "Some Properties of Peroxidases of Healthy and Botrytiscinera–Infected Cabbage Tissues".
Ellis, M. B., *Principal Mycologist Commonwealth Mycological Institute,* Kew, England, 8-15 (1976), "More Dematiacous Hypomycetes".
Lilly, V. G. and Barnett, H. L., 425-429 (1951) in "Physiology of the Fungi", 1st Edition, 1951, McGraw-Hill, N.Y.
Pansy, F. E. et al., *Antimicrobial Agents and Chemotherapy,* 399 (1967).
Hager, L. P. et al., *The Journal of Biological Chemistry,* 1769-1777 (1966).
Morrison, Martin and Schonbaum R. Gregory, *Ann. Rev. Biochem.,* 45:861-874 (1976).
Mullen, A., *Klaus Weissermel Hans-Jurgen Arpe,* pp. 127-129 and 260-261 (1978) in "Industrial Organic Chemistry", Verlag Chemie, N.Y., 1978.
Ellis, M. B., *Commonwealth Mycological Institute,* Kew, England 7-23 (1971) in "Dematiaceous Hypomycetes".

*Primary Examiner*—Thomas G. Wiseman
*Assistant Examiner*—Robin Lyn Teskin
*Attorney, Agent, or Firm*—Albert P. Halluin; Jane McLaughlin; Virginia Meyer

[57] ABSTRACT

A halogenation method using a haloperoxidase obtained from a fungus selected from the dematiaceous hyphomycetes. The enzyme has an optimum activity above about pH 5.0, and can oxidize chloride, bromide, or iodide ions.

15 Claims, No Drawings

FUNGAL CHLOROPEROXIDASE METHOD

BACKGROUND AND SUMMARY

The present invention relates to a chloroperoxidase enzyme preparation, and in particular, to a fungal chloroperoxidase enzyme preparation having a pH optimum above pH 5.0 and the ability to oxidize chloride, bromide, and iodide ions.

There has been considerable interest in recent years in enzymatic halogenation. U.S. Pat. Nos. 4,247,641 and 4,284,723 describe the use of haloperoxidase enzymes to produce epoxides from alkenes. Other recent research activity in this field has involved the use of haloperoxidase enzymes to produce halogenated ketones from alkynes, to produce alpha, gamma-halohydrins from cyclopropanes, and to produce dihalogenated products from alkenes and alkynes. The term haloperoxidase is used herein to include chloroperoxidases, bromoperoxidases, and iodoperoxidases. A chloroperoxidase, as that term is used herein, is an enzyme capable of oxidizing chloride, bromide, or iodide ions with the consumption of $H_2O_2$. A bromoperoxidase can oxidize iodide and bromide, but not chloride ions, and an iodoperoxidase can oxidize iodide ions only, both of the latter enzymes requiring $H_2O_2$ as a substrate.

Haloperoxidase enzymes which are known in the prior art and which have been used in halogenation-reaction studies include chloroperoxidase derived from the fungus *Caldariomyces fumago*, bromoperoxidase from algae, lactoperoxidase from milk, thyroid peroxidase from the thyroid, myeloperoxidase from leukocytes and horseradish peroxidase from horseradish. These enzymes are described generally in the Morrison, et al., *Ann. Rev. Biochem.*, 45, 861 (1976).

Many industrial applications of halogenation involve chloride ions. The conversion of propylene to propylene oxide via chlorohydrin, described in Weissermel et al., in *Industrial Organic Chemistry*, 128, 260, (1978) is one example. Therefore, it is often advantageous that the haloperoxidase enzyme used in industrial halogenation be able to oxidize chloride ions.

Of the several known haloperoxidases which are mentioned above, only myeloperoxidase derived from leukocytes and chloroperoxidase from *C. fumago* are able to utilize chloride ions. A limitation of the *C. fumago* chloroperoxidase, in industrial applications, is that the enzyme has a pH optimum of around 3, and has relatively low activity and stability above pH 7.0. Thus, the enzyme preparation obtained by fermentation must first be acidified, and after product formation, the acid must be neutralized by the addition of base for product recovery or further conversion. The two pH adjustments significantly increase the cost of the halogenation reaction. Myeloperoxidase from leukocytes operates in the desired neutral pH range, but the enzyme is not readily obtained in quantities suitable for industrial use, as seen in U.S. Pat. No. 4,379,141, issued Apr. 5, 1983.

It is one object of the present invention, therefore, to provide a haloperoxidase enzyme which combines important commercial advantages not found in any single haloperoxidase known heretofore.

A more specific object of the invention is to provide such an enzyme which is readily obtained by fermentation, has a pH optimum above about pH 5.0, and can utilize chloride ions.

It is still another object of the invention to provide a method of enzymatically halogenating a compound, at a selected pH between about 4 and 9, inclusive, using a fungal haloperoxidase derived from a fungus selected from the dematiaceous hyphomycetes.

A further object of the invention is to provide a method of oxidizing iodide ions enzymatically to molecular iodine.

Still another object of the invention is to provide a method of preparing such a haloperoxidase enzyme.

The invention includes a method for producing a halogenating enzyme which has a pH optimum above about pH 5.0, and which can oxidize chloride, bromide, or iodide ions in the presence of $H_2O_2$. The method involves selecting a fungus from the dematiaceous hyphomycetes, and deriving from the selected fungus, an enzyme capable of brominating phenol red and halogenating monochlorodimedon in the presence of the appropriate halide and $H_2O_2$ at a pH typically between about 7.0 and 8.5. Preferred organisms are selected from one of the genera including Alternaria, Curvularia, Drechslera, Ulocladium in the enteroblastic tretic group of dematiaceous hyphomycetes, and Botrytis in the acroauxic holoblastic group.

The enzyme is used in halogenating, at a selected pH between about 4 and 9, a compound preferably selected from the group consisting of alkenes, alkynes, cyclopropanes, beta-keto acids, cyclic beta-diketones and aromatic ring compounds. Preferred compounds include ethylene, propylene, monohalogenated analogues of these alkenes, and allyl alcohol.

These and other objects and features of the present invention will become more fully apparent from the following detailed description of the invention.

DETAILED DESCRIPTION OF THE INVENTION

According to the method of the invention, a fungus selected from the dematiaceous hyphomycetes is used to produce a haloperoxidase enzyme capable of oxidizing chloride, bromide, or iodide ions at a neutral or near-neutral pH. The structure classification of dematiaceous hyphomycetes follows that described in Ellis, M.B., *Dematiaceous Hyphomycetes*, pp. 7–23, Commonwealth Mycological Institute, Kew, Surrey, England, (1971) and in Ellis, M.B., *More Dematiaceous Hyphomycetes*, pp. 8–15, Commonwealth Mycological Institute, Kew, Surrey, England (1976). As outlined therein, the dematiaceous hyphomycetes can be divided into six groups based on characteristic morphology. The six groups are listed in Table I, the number of classified genera in each group being indicated in parentheses beside the group name.

TABLE I

| | No. of Genera | Group No. |
|---|---|---|
| Thallic | | |
| Non-meristematic | (12) | #1 |
| Meristematic | (2) | #2 |
| Blastic | | |
| Basauxic | (6) | #3 |
| Acroauxic | | |
| Holoblastic | (262) | #4 |
| Enteroblastic | | |
| Tretic | (36) | #5 |
| Phialidic | (51) | #6 |

According to one aspect of the invention, a fungus selected from one of the six above-identified dematiaceous hyphomycete groups is cultured under conditions which are selected to optimize the measured haloperoxidase activity produced by the fungus. In a preferred protocol used in culturing the selected fungus, a small block from a sporulating fungal slant is transferred aseptically to a fungal agar seed plate and incubated at room temperature for a period typically between about 3 to 7 days. The fungal agar used in the seed plate is selected to produce optimal fungal spore mass after the 3 to 7 day growth period. Details of the agar-selection method, including the compositions of several fungal agars used, are given below in Example I.

Following the growth of the selected fungus on a seed plate, a uniform segment of mycelium and spores is removed and aseptically transferred to a flask containing a selected germination broth which may include a small amount of agar added to prevent mycelial clumping and pellet formation. The flask is shaken for several days, typically between about 3 to 5 days, at room temperature. The particular germination broth which is selected is that which produces optimal biomass after the 3 to 5 day incubation period. Specific procedures used in germinating various fungal species in selected germination broths are described in Example II.

At the end of the germination period, an aliquot of germination broth is transferred into a flask containing a selected fermentation broth. The selected broth is that which has been found, by earlier testing, to produce an optimal biomass after a 5 to 9 day incubation period in the fermentation broth at 25° C. The formulations of several fermentation broths used herein are described below in Example III.

After the addition of an aliquot of fungal material from the germination broth to a flask containing the selected fermentation broth, the contents of the flask are incubated by shaking at a selected temperature for a period of typically between about 5 and 9 days. The incubation temperature selected is that which produces the highest measurable haloperoxidase enzyme activity in the fermentation broth at the end of the incubation period. In one preferred protocol, described in Example IV below, the fungus is incubated in the selected fermentation broth at a temperature of either 19° C., 25° C., or 34° C.

The incubation of the fungus in the selected fermentation broth, at the selected temperature is allowed to proceed over a several-day period until a maximal measurable haloperoxidase enzyme activity in the broth is observed. As noted above, this incubation period ranges typically from 5 to 9 days. However, for certain selected fungi, and particular, those in the Botrytis genus in the acroauxic holoblastic group of dematiaceous hyphomycetes, a fermentation period of up to 12 to 15 days may be required to produce maximal haloperoxidase activity levels.

At the end of the fermentation period, the fungal culture is assayed for its ability to brominate phenol red in the presence of $H_2O_2$ and bromide ions. In the assay, which is also referred to herein as a phenol red assay, a substrate reagent containing phenol red, a bromide salt, and freshly prepared $H_2O_2$ is added directly to the fermentation medium. The reaction is carried out at a selected temperature between 19° C. and 34° C. for a period of between 1 and 24 hours. Bromination of phenol red is evidenced by a color change from red-orange to blue-violet. The extent of color change is noted one hour after the addition of reagent. Thereafter, depending on the extent of color change which is observed, fresh $H_2O_2$ is added at 1, 3, 5, and 8 hours after the initiation of the reaction, and the extent of color change is monitored at hours 2, 4, 6, 9 and 24. Haloperoxidase activity in the growth medium can be quantitated by following the reaction spectrophotometrically at 595 nm. For the spectrophotometric determination, the fermentation broth is centrifuged to remove fungal cells and the optical density of the supernatant is measured with respect to diluted fermentation broth supernatant containing $H_2O_2$ but no phenol red.

Organisms which were found to be haloperoxidase positive in the phenol red assay just described were further tested for the ability to chlorinate monochlorodimedon (1 1, dimethyl-4-chloro-3, 5, cyclohexanedione) to dichlorodimedon in the presence of chloride ions and $H_2O_2$ as described by Hager, P., Morris, D. R., Brown, F. S., and Aberwein, H., *J. Biol. Chem.*, 241:1769–1777 (1966). This test is also referred to herein as an MCD assay.

Both assays indicate the presence, in the system being tested, of an enzyme capable of catalyzing the oxidation of a halide with $H_2O_2$, to give the corresponding hypohalous acid. The hypohalous acid may further react with and halogenate selected acceptor compounds, or may react with the halide to produce the corresponding halogen.

Approximately 112 fungal organisms selected from the dematiaceous hyphomycetes were tested for haloperoxidase activity according to the culturing and enzyme-assay methods outlined above. The organisms tested were grouped into one of four classes depending on the level of enzyme activity in the phenol red assay. High-activity producers (class 1) included those having a bromination activity level which produced an optical density (OD) reading, one hour after addition of the phenol red reagent, of 1.2 or greater. About 32 of the 112 fungal organisms tested are in this class of high-activity producers. The organisms in this class which were tested in the MCD assay showed high activity. A partial list of the high-activity producers and the culture conditions used to obtain maximal haloperoxidase activity levels are described in Example VI below.

Moderate-activity haloperoxidase producers (class 2) were characterized by their ability to brominate phenol red at a level which produces an optical density reading between 0.5 and 1.2, after an assay reaction period of between 1 and 24 hours. The organisms in the second class which were tested in the MCD assay showed correspondingly lower activity than the class 1 organisms. Approximately 21 of the 112 organisms tested are in the second class. Representative organisms in this class, and the culture conditions used to obtain maximal haloperoxidase activity levels are described in Example VII.

A third group of haloperoxidase producers were characterized as having a bromination activity level which gave an OD reading of less than 0.5 in the phenol red assay, after a 24 hour reaction period. The organisms in the third class which were tested in the MCD assay showed low activity. About 30 of the 112 organisms tested were in the third class.

A fourth group of fungal organisms tested showed no measurable bromination activity after a 24 hour assay reaction period.

The relatively low haloperoxidase levels observed for Class 2 and 3 organisms may be due, in some cases, to relatively high levels of catalase or other peroxide-decomposing enzymes produced by some organisms in these classes. The catalase would act to reduce measurable haloperoxidase activity by the reducing substrate $H_2O_2$ concentration, an effect which would be partially overcome by the periodic addition of $H_2O_2$ to the reaction, over a reaction period of up to 24 hours.

Table II below lists the dematiaceous hyphomycetes which were found, according to the above selection procedures, to produce high, moderate or low activity levels of haloperoxidase, as evidenced by the bromination of phenol red after a 1-24 hour reaction period, and/or by the chlorination of monochlorodimedon. The list includes 83 of the total of 112 organisms tested. The dematiaceous hyphomycete organisms tested were obtained from a variety of sources. Many of the species were obtained from cultured collections including the Institute for Fermentation, Osaka (IFO); Quarter Master Culture Collection (Natick) (QM), presently located at the University of Massachusetts, Amherst, Mass.; American Type Culture Collection (ATCC) Centraalbureau voor Schimmelcultures (CBS); Northern Regional Research Laboratory (NRRL); and Cetus Master Culture Collection (CMCC). Other dematiaceous hyphomycetes species were obtained from various decaying material, via inplant and outgrowth techniques, on selected fungal-isolation agar. The organisms obtained were identified according to their characteristic morphology, consistent with the classification scheme detailed in the above-noted references to Ellis. For a number of organisms and particularly those derived from soil samples, it was impossible to make a species identification, because the organism's natural host was not known. These organisms are given the species designation "sp." herein.

The numbers in parentheses at the right in Table II indicate the number of separate organisms of each designated genus and species that was tested and found to be haloperoxidase-positive. Where organisms are positively identified as to the same genus and species, the separate organisms tested were obtained from different sources and presumed to be distinct strains of the same species. Where no species identification could be made, the separate organism tested were also obtained from different sources, and may include distinct species or distinct strains within a species. The organisms are listed according to their grouping in the 6 dematiaceous hyphomycete groups defined in Table I.

TABLE II

| #1 Thallic Non-Meristematic | |
|---|---|
| *Wallemia Sebi* | (1) |
| #2 Thallic Meristematic | |
| None Found | |
| #3 Blastic Basauxic | |
| None Found | |
| #4 Acroauxic Holoblastic | |
| *Bispora betulina* | (2) |
| *Botrytis cinerea* | (1) |
| *Botrytis sp.* | (3) |
| *Cladosporium cladosporioides* | (1) |
| *Cladosporium resinae* | (2) |
| *Cladosporium sphaerosperum* | (1) |
| *Cladosporium sp.* | (3) |
| *Epicoccum nigrum* | (1) |
| *Helicoma isiola* | (1) |
| *Humicola fuscoatra* | (2) |
| *Stemphyllium macrosporidium* | (1) |
| *Wardomyces anomalus* | (1) |
| #5 Enteroblastic Acroauxic Tretic | |
| *Alternaria alternata* | (2) |
| Alternaria, form of *Pleospora infectoria* | (1) |
| *Alternaria sp.* | (13) |
| *Drechslera sp.* | (4) |

TABLE II-continued

| *Curvularia cymbopogonis* | (1) |
|---|---|
| *Curvularia inaequalis* | (2) |
| *Curvularia lunata* | (1) |
| Curvularia, state of *Cochliobolus geniculata* | (1) |
| *Curvularia tuberculata* | (1) |
| *Curvularia verruciformis* | (1) |
| *Curvularia sp.* | (10) |
| *Dendryphiella salina* | (1) |
| *Dendryphion nanum* | (1) |
| *Dichotomphthora portulacae* | (1) |
| *Drechslera halodes* | (1) |
| Drechslera, state of *Chocliobolus sativa* | (3) |
| *Embellisia allii* | (2) |
| *Embellisia sp.* | (2) |
| *Ulocladium chartarum* | (4) |
| *Ulocladium sp.* | (10) |
| #6 Enteroblastic Phialidic | |
| *Aspergillus niger* | (1) |
| *Gliocephalotrichum sp.* | (1) |
| *Stachybotrys sp.* | (1) |

As seen in Table II, all but 4 of the 83 haloperoxidase-producing fungal species identified according of the invention are in either the acroauxic holoblastic group or enteroblastic tretic group. Further, all of the fungal organisms identified as being high-level haloperoxidase producers, and all but one identified as being moderate-level haloperoxidase producers are in the fourth or fifth groups. Of these two groups, 62 haloperoxidase producers are in the enteroblastic tretic group compared with 14 in the acroauxic holoblastic group. As will be seen in Example VI below, almost all of the high-haloperoxidase producers are in one of the group 5 genera including Alternaria, Curvularia, Drechslera, and Ulocladium and Botrytis in group 4.

The foregoing discloses how a fungal organism which produces a chloroperoxidase which functions at or above pH 5.0 can be selected. According to another important aspect of the invention, the chloroperoxidase produced may be used in a variety of haloperoxidase reactions having commercial applicability. Typically, the haloperoxidase is used in such reaction in a purified or partially purified form. Enzyme purification may be accomplished, according to the preferred procedure in the present invention, by disrupting and filtering the contents of the fermentation flask, and making selective ammonium sulfate cuts to increase the purity of the enzyme. The purification procedure produces a several-fold increase in the measured specific activity of the haloperoxidase enzyme over that in the crude filtrate.

The purified or partially purified halogenating enzyme may be used in free or immobilized form. Processes for enzyme immobilization are well known, and include reacting a solution of the enzyme with one of a broad range of organic or inorganic supports. Included among these are polyacrylamide, ethylene-maletic acid copolymers, agarose, cellulose, dextran, porous glass beads, and aluminum or titanium hydroxide. Enzymes in this form have increased stability, extended life, and recoverability. Reactions employing immobilized enzymes may be run in columns or reaction tanks.

Alternatively, the halogenating enzyme may be provided as a suspension of undisrupted cells (including spores and mycelia) or contained in cells immobilized on a solid support. Both of the above assay reactions occur readily when substrates (e.g., phenol red or monochlorodimedon) are added to intact cells in the presence of $H_2O_2$ and an appropriate halide salt such as those present in seawater. Important advantages of using undisrupted cells as a source of fungal chloroperoxidase are increased enzyme stability and simplicity of enzyme preparation.

Another advantage of using undisrupted cells is that the haloperoxidase reaction may be carried out at a pH of about 9.0, where the activity of the isolated enzyme is suboptimal. Thus, the method of the invention is well suited to processes in which the haloperoxidase-catalyzed reaction product is further reacted under basic pH conditions. By way of illustration, U.S. Pat. No. 4,247,641 discloses a method of producing epoxides from alkenes by reacting an alkene with a haloperoxidase to form a halohydrin, and treating the halohydrin with a base to produce the epoxide. The present invention contemplates a method of forming industrially important epoxides by halogenating alkenes enzymatically at a pH at which the enzymatically formed halohydrin spontaneously forms the desired epoxide.

The chloroperoxidase described herein is obtained directly from a selected fungal organism. The invention also contemplates a reaction method using a chloroperoxidase that is produced by a microorganism, e.g., a bacterium, that has received by recombinant DNA techniques, fungal genetic material requisite for the synthesis of the fungal chloroperoxidase.

The chloroperoxidase enzyme fraction provided is used for halogenating, at a selected pH between about 4.0 and 9.0, a compound susceptable to haloperoxidase-catalyzed halogenation. Typical compounds include alkenes, alkynes, cyclopropanes, beta-keto acids, cyclic beta-diketones, and aromatic ring compounds. Specific example of organic compounds which can be halogenated via enzymatic oxidation of halide ions in the presence of $H_2O_2$ are well known to those skilled in the art and will not detailed here. Preferred among the acceptor compounds are ethylene, allyl chloride, propylene, and allyl alcohol. Depending on the composition and concentration of halide ions in the reaction medium, the haloperoxidases of the invention may produce halohydrins or dihalogenated products, including mixed halogen products. Examples IX–XIII below detail such reactions.

The compound to be halogenated is reacted with the fungal chloroperoxidase in the presence of $H_2O_2$ and either chloride, bromide or iodide ions. The $H_2O_2$ may be generated in situ, for example, by the reaction of glucose with a glucose oxidase. The reader is referred to U.S. Pat. Nos. 4,246,347; 4,247,641; and 4,284,723 for reaction methods involving $H_2O_2$ generation. The reaction medium preferably includes a buffer whose pH is adjusted to a selected pH between 4.0 and 9.0. The reaction may be carried out at room temperature or at a selected optimal temperature under atmospheric pressure for a period of up to several hours.

Many of the acceptor compounds may be gaseous and/or sparingly soluble in aqueous solution. Gaseous compounds may be bubbled through the solution. Sparingly soluble compounds may be dispersed in the reaction medium by rapid stirring, and the compounds may be made more soluble by the addition to the reaction medium of non-aqueous solvents such as dimethyl sulfoxide or ethanol.

The enzyme fraction may also be employed in a reaction method for oxidizing iodide ions to molecular iodine in the pH 4–9 range, as seen in Example XIII.

The following examples serve to illustrate the invention further and are not intended to limit the scope of the invention.

EXAMPLE I

Growlh of selected dematiaceous hyphomycetes on agar seed plates

The growth of four selected dematiaceous hyphomycetes on seed plates containing various fungal agars was studied. The four organisms were (1) Botrytis sp., NRRL #15309; (2) *Alternaria alternata*, NRRL #15150; (3) *Curvularia inaequalis*, NRRL #15147; and (4) Drechslera sp., NRRL 15146.

For each of the fungal species, a small block from a sporulating slant was aseptically cut out and placed face down on the dry surface of a fungal agar seed plate containing one of the following four different fungal agars:

PDA agar was prepared by adding potato dextrose agar (39.0 g) (DIFCO) to 1 liter of distilled water.

FA agar was prepared by adding glucose (15.0 g), yeast extract (3.0 g), agar (20.0 g), and artificial sea water (1 ml: Aquarium Systems, Eastlake, Ohio) to 966 ml of distilled water (Barnett and Lilly, *Physiology of the Fungi* (1951)). The preparation was autoclaved at 15 psi for 15 minutes, after which thiamine (100 micrograms) and biotin (5 micrograms) were added via filter sterilization. Final pH was between 6.0 and 6.5.

$H_2O$ agar was prepared by adding crude flake agar (Meer Corp.) (17.5 g) to 1 liter of distilled water.

V-8 agar was prepared by adding V-8 Cocktail Vegetable Juice (Campbell Soup Co.) (200 ml), $CaCO_3$ (3.0 g), and agar (15.0 g) to 800 ml tap water.

Each seed plate was incubated at 25° C. until growth of the spore mass was essentially complete, typically between about 3 and 7 days. Table III below indicates the particular fungal agar, identified as above, which produced optimal spore mass for each of the four different organisms.

TABLE III

| Organism | Fungal Agar |
|---|---|
| Botrytis sp. | PDA |
| A. alternata | FA |
| C. inaequalis | $H_2O$ or FA |
| Drechslera sp. | V-8 |

EXAMPLE II

Growth of selected dematiaceous hyphomycetes in different germination broths

Each of the four selected organisms from Example I was grown on an agar seed plate containing the selected fungal agar indicated in Table I. A segment of mycelium and spores was transferred aseptically from the seed plate into a 250 ml Erlenmeyer flask containing 50 ml of one of three different germination broths, whose composition is as follows:

CF germination broth was prepared by adding potato-dextrose broth (24.0 g), yeast extract (3.0 g) agar (0.2 g) and 1 ml of the above artificial sea water to 1 liter of distilled water.

FA germination broth was identical to FA fungal agar, except that the germination broth contained a final agar concentration of 0.02%.

FP germination broth was prepared by adding tryptone (5.0 g), malt extract (3.0 g), glucose (10.0 g), yeast extract (3.0 g) and agar (0.2 g) to 1 liter of distilled water (Pansey et al., *Antimicrob. Agents Chemother.*, 399 (1966)). Agar was added the germination broths to prevent mycelial clumping and pellet formation.

After transfer of the mycelium and spores to the flasks containing the different germination broths, the flasks were shaken on a New Brunswick Rotary Shaker for 3 to 5 days at 200 rpm in a 25° C. room. If a gelatinous pellet formed on incubation, the material was harvested and ground aseptically to a mushy or applesauce consistency in a sterile Waring Blender for 5–30 seconds in short (5 second) bursts. The growth material was diluted with sterile distilled water to 5% (v/v) inoculum.

Table IV below indicates, for each of the four fungal organisms tested, the germination broths which produced the greatest biomass in the 3–5 day incubation period.

TABLE IV

| Organism | Germination Broth |
| --- | --- |
| Botrytis sp. | FP |
| A. alternata | CF |
| C. inaequalis | FA or CF |
| Drechslera sp. | FA |

EXAMPLE III

Growth of the selected fungal organisms in different fermentation broths

For each of above fungal organisms, an inoculum formed in accordance with Example II was transferred aseptically to 15 ml of one of three different fermentation broths contained in a 125 Erlenmeyer flask. The three different fermentation broths, designated CF, FA and F4, were identical to same-named germination broths, but contained no agar. The fermentation flasks containing the fungal inocula were shaken at 200 rpm on a rotary shaker at 25° C. After an incubation period of at least 5 days, the contents of each flask were assayed for the ability to brominate phenol red in the presence of $H_2O_2$ and a halide salt, as will be detailed below in Example V. For each of the four fungal organisms, the fermentation broth which produced the highest bromination activity level at the end of the fermentation period was noted, as reported in Table V.

TABLE V

| Organism | Fermentation Broth |
| --- | --- |
| Botrytis sp. | F4 |
| A. alternata | CF |
| C. inaequalis | CF |
| Drechslera sp. | CF |

EXAMPLE IV

Growth of the selected fungal organisms in optimal fermentation broth at selected temperatures The best fermentation broth of each of the four selected fungal organism was determined in accordance with Example III above. An inoculum of each selected fungus prepared from germination medium in accordance with Example II was transferred aseptically to 15 ml of the selected optimal fermentation broth contained in each of three 125 ml Erlenmeyer flasks. The flasks were shaken at 200 rpm on a Brunswick rotary shaker at either 19° C., 25° C., or 34° C. After 5 days of incubation, an aliquot from each of the 3 different-temperature fermentation media was assayed for activity level in brominating phenol red at 25° C. This procedure was repeated successively on each following day until a maximum brominating activity level was observed.

Table VI shows, for each of the fungal organisms studied, the fermentation-growth temperature which produced the highest bromination activity level for each organism. The number of days of incubation at the designated temperature is indicated at the column in the right in Table VI.

TABLE VI

| Organism | Temp. | pH | day |
| --- | --- | --- | --- |
| Botrytis sp. | 25° C. | 7.0 | 15 |
| A. alternata | 34° C. | 8.0 | 6 |
| C. inaequalis | 25° C. | 7.0 | 8 |
| Drechslera sp. | 25° C. | 8.0 | 7 |

The pH of the fermentation broth which was measured at the end of the incubation period is indicated in the middle column in Table VI.

As seen from the table, the length of fermentation, at the optimal temperature, which produced maximum observable bromination activity level ranged between about 7 and 15 days. The pH of each of the fermentation measured at the end of the incubation period, was between 7.0 and 8.0.

EXAMPLE V

Measurement of bromination and chlorination activity levels

The bromination activity level in each of the fermentation broths was determined by mixing a phenol red regeant with an equal volume of material from the fermentation flasks. The phenol red reagent was prepared by adding 40 ml of 0.2% phenol red in 95% ethanol to 1 liter of 0.3M $KPO_4$, and 0.5 KBr. The pH was adjusted to 7.0 with KOH. Fifteen ml of the reagent were added directly to 15 ml of the contents of the fermentation flask. A 0.02 ml aliquot of freshly prepared 3.0% $H_2O_2$ was added to start the reaction, which was performed at a selected temperature for one to 24 hours. At the end of the reaction period, the reaction mixture was centrifuged to pellet fungal cells and the optical density of the supernatant was read spectrophotometrically at 595 nm using as a reference, the supernatant of fungal growth diluted one-to-one with buffer and $H_2O_2$. The bromination activity level in fungal cultures grown in accordance with the method of Example IV, produce an optical density reading of greater than about 1.2 for each of the fungal organisms tested in that example.

Each of the fungal organisms which was found to have a high bromination activity level was tested for its ability to chlorinate monochlorodimedon in the presence of a chloride salt and added $H_2O_2$. A reaction mixture containing 30 mM KCl, 0.3M $KPO_4$, pH 5.0, 10 mM $H_2O_2$ and 20 mM monochlorodimedon was prepared. Fermentation growth medium was centrifuged to remove fungal cells and the supernatant was added to an equal volume of the monochlorodimedon reaction mixture. The reaction, which was carried out over a period of five minutes at room temperature, was followed spectrophotometrically by the conversion of monochlorodimedon, which has a strong absorption at 277 nm, to dichlorodimedon, which has a very weak absorption at this wavelength. Each of the four fungal organisms from Examples I–IV showed high chlorination activity level in the monochlorodimedon test.

EXAMPLE VI

Selection of dematiaceous hyphomycete capable of producing high activity levels of chloroperoxidase Selected fungal organisms from the dematiaceous hyphomycetes were grown under optimal growth conditions according to the results from Example I–IV, and tested for chloroperoxidase activity, to select for organisms producing high activity levels of chloroperoxidase. Of the approximately 112 distinct species or strains of dematiaceous hyphomycetes which were tested, 33 were found to be high chloroperoxidase producers by the criterion that the phenol-red assay produced an optical density of 1.2 or greater after one hour reaction at 25° C. A partial list of the organisms which produced high levels of chloroperoxidase is given in Table VII, along with the deposit numbers of the organisms and the dematiaceous hyphomycete group number. All of the high-producer organisms which were tested in the MCD assay gave good activity.

The unspeciated fungal organism in the Botrytis, Drechslera, and Ulocladium genera listed below were characterized according to their observed morphology. Morphological observations were made from cultured material, tweezed out on water-mounted slides, and observed through a Zeiss Universal transmitted light microscope at 500× and 1250×, as follows:

Botrytis sp., CMCC #0253. Colonies light gray. No schlerotia formed; Conidia 6–12 microns (mostly 8–10 microns)×10–24 microns (mostly 12–14 microns); Non-sporulating Ascomycete stage present. Host unknown.

Botrytis sp., CMCC #0256. Colonies light gray. Weak sporulation on V-8 fungal agar. No schlerotia formed in culture. Conidia 8–10 microns ×12–20 microns (mostly 12–14 microns). Host unknown.

Botrytis sp., CMCC #1293. Colonies gray. Abundant sporulation on V-8 fungal agar. Numerous sclerotia formed in culture. Conidia 8–12 microns (mostly 10 microns) ×12–20 microns (mostly 14–16 microns). Phialidic stage present. Isolated from grapes.

Drechslera sp., CMCC #0834. Colonies black. Hilium non-protuberant. Conidia 6–10 microns ×18–36 microns, ellipsoidal to cylindrical with rounded ends. Five pseudosepta. Host unknown. Isolated from British Virgin Island soil sample.

Drechslera sp., CMCC #0835. Colonies black. Hilium non-protuberant. Conidia 8–18 microns (mostly 10–12 microns) ×22–42 microns (mostly 28–38 microns), ellipsoidal to cylindrical. Conidia smooth with 3–7 but mostly 5 pseudosepta. Conidiphore smooth and unbranched. Host unknown. Isolated from British Virgin Island soil sample.

Drechslera sp., CMCC 1302. Colonies black; Hilium non-protuberant. Conidia 8–10 microns (mostly 10 microns) ×24–44 microns (mostly 24–30 microns), fusiform to cylindrical, five pseudosepta. Host unknown.

Drechslera sp., CMCC #1290. Colonies black. Hilium non-protuberant. Conidia straight; 50–96 microns (mostly 70–76 microns) ×14–20 microns (mostly 16–18 microns); ellipsoidal, sometimes tapering ends. Natural substrata unknown. Isolated from New Jersey soil sample.

Ulocladium sp., CMCC #1291. Colonies golden brown to mustard. Conidia mostly solitary, but short chains common. Conidia smooth to verrucose or rough. Mostly spherical or cruciform to obovate with 1–3 transverse septa and 0–2 oblique septa. Golden brown. 16–30 microns (mostly 11–12 microns) ×18–30 microns mostly 24–30. Conidiophores golden and smooth. Isolated from South American soil sample.

Ulocladium sp., CMCC #1292. Colonies golden brown to olive with white cottony mucelia on FA fungal agar. Conidia solitary, but short chains common. Conidia smooth to rough; mostly obovate to spherical, with 1–3 tansverse septa and 0–3 oblique septa. Golden to dark brown, 10–24 microns (mostly 14–16 microns) ×18–38 ×(mostly 26–30 microns). Conidiophores golden and smooth. Isolated from South American soil sample.

Ulocladium sp., CMCC #1300. Colonies golden brown, becoming almost black. Conidia solitary, rarely in chains. Conidia verrucose to warty; diameters 16–32 microns (mostly 20–24 microns). Golden brown. Conidiophore golden and smooth. Isolated from South American soil sample.

Ulocladium sp., CMCC #1301. Colonies dark olive green. Conidia mostly solitary, occacionally in short chains. Conidia mostly spherical to subspherical, smooth to somewhat roughened. Golden brown; diameters 12–22 microns (mostly 14–16 microns). Conidiophores smooth and golden brown. Isolated from Death Valley soil sample.

TABLE VII

| GENUS/SPECIE | CMCC # | OTHER # | NRRI # | GROUP |
|---|---|---|---|---|
| Alternaria alternata | 1286 | | 15150 | 5 |
| Alternaria alternata | 1288 | | 15291 | 5 |
| Alternaria alternata | 0514 | | 15289 | 5 |
| Curvularia cymbopogonis | 0850 | ATCC 38580 | | 5 |
| Curvularia inaequalis | 1262 | ATCC 14992 | | 5 |
| Curvularia inaequalis | 0755 | | 15147 | 5 |
| Curvularia lunata | 0843 | ATCC 12017 | | 5 |
| Curvularia tuberculata | 0842 | ATCC 15058 | | 5 |
| Curvularia verruciformis | 0844 | QM 8326 | | 5 |
| Curvularia lunata | 1296 | | 15293 | 5 |
| Curvularia lunata | 1297 | | 15196 | 5 |
| Dichotomophthora portulacae | 1283 | CBS 239.48 | | 5 |
| Drechslera halodes | 1299 | | 15151 | 5 |
| Drechslera sp. | 0834 | | 15290 | 5 |
| Drechslera sp. | 0835 | | 15146 | 5 |
| Drechslera sp. | 1302 | | 15294 | 5 |
| Drechslera sp. | 1290 | | 15197 | 5 |
| Ulocladium sp. | 0282 | | 15200 | 5 |
| Ulocladium sp. | 1291 | | 15201 | 5 |
| Ulocladium sp. | 1292 | | 15102 | 5 |
| Ulocladium sp. | 1300 | | 15103 | 5 |
| Ulocladium sp. | 1301 | | 15104 | 5 |
| Botrytis cinerea | 0311 | | 15327 | 4 |
| Botrytis sp. | 0253 | | 15326 | 4 |
| Botrytis sp. | 0256 | | 15309 | 4 |
| Botrytis sp. | 1293 | | 15292 | 4 |

As noted, each organism which was tested was grown under conditions which optimize chloroperoxidase production, in accordance with methods described in Examples I–IV. Thus, the particular fungal agar which was selected for each organism was that which produced optimal spore mass over a 3–7 day incubation period at 25° C. The germination broth selected was that which produced maximal biomass after a 5–9 day germination period at 25° C., and the fermentation broth selected was that which produced optimal activity levels in the phenol-red bromination assay at 25° C. The fermentation temperature in the selected fermentation broth, was that which produced optimal activity levels in the phenol red bromination assay, and the length of the fermentation was extended until the maximum activity level was observed. The particular fungal agar, germination broth, fermentation borth, fermentation temperature, and fermentation period for each of the organisms listed in Table VII are shown in Table VIII.

TABLE VIII

| ORGANISM | CMCC # | AGAR | GERM. | FERM. | TEMP. | pH | DAY |
|---|---|---|---|---|---|---|---|
| A. alternata | 1286 | FA | CF | CF | 34 | 7.60 | 6 |
| A. alternata | 1288 | FA | FA | CF | 34 | 7.65 | 8 |
| A. alternata | 0514 | FA | FA | F4 | 25 | 8.12 | 7 |
| C. cymbopogonis | 0850 | $H_2O$ | F4 | F4 | 19 | 8.40 | 6-8 |
| C. inaequalis | 1262 | $H_2O$ | FA | F4 | 25 | 8.52 | 7 |
| C. inaequalis | 0755 | FA/$H_2O$ | FA | CF | 25 | 8.26 | 7 |
| C. lunata | 0843 | $H_2O$ | F4 | F4 | 25 | 8.35 | 8 |
| C. tuberculata | 0842 | $H_2O$ | F4 | F4 | 34 | 8.12 | 9 |
| C. verruciformis | 0844 | $H_2O$ | F4 | F4 | 34 | 8.43 | 8 |
| C. lunata | 1296 | FA | F4 | F4 | 25 | 8.68 | 6 |
| C. lunata | 1297 | $H_2O$ | F4 | F4 | 25 | 8.57 | 8 |
| D. portulacae | 1283 | $H_2O$ | F4 | F4 | 25 | 7.96 | 6 |
| D. halodes | 1299 | $H_2O$ | FA | FA | 25 | 8.33 | 7 |
| Drechslera sp. | 0834 | V8 | F4 | F4 | 25 | 6.50 | 9 |
| Drechslera sp. | 0835 | V8 | FA | CF | 25 | 8.36 | 8 |
| Drechslera sp. | 1302 | FA | F4 | F4 | 25 | 8.49 | 6 |
| Drechslera sp. | 1290 | V8 | CF | F4 | 34 | 7.60 | 6 |
| Ulocladium sp. | 0282 | V8 | FA | FA | 19 | 8.40 | 7 |
| Ulocladium sp. | 1291 | V8 | FA | FA | 34 | 7.72 | 7 |
| Ulocladium sp. | 1292 | V8 | FA | CF | 25 | 7.80 | 8 |
| Ulocladium sp. | 1300 | V8 | FA | CF | 34 | 7.42 | 6-7 |
| Ulocladium sp. | 1301 | V8 | FA | CF | 25 | 7.79 | 7 |
| B. cinerea | 0311 | PDA | F4 | F4 | 25 | 5.30 | 13 |
| Botrytis sp. | 0253 | PDA | F4 | F4 | 25 | 7.00 | 15 |
| Botrytis sp. | 0256 | PDA | F4 | F4 | 25 | 7.30 | 12 |
| Botrytis sp. | 1293 | FA | F4 | F4 | 25 | 8.60 | 8 |

Also listed in Table VIII, in the second column from the right, is the pH of the fermentation broth, measured at the end of the fermentation period. It can be appreciated from the table that all but one (B. cinerea) of the high-activity producers were characterized by a fermentation broth pH of between about 6.5 and 8.5. Further, the length of fermentation needed to produce optimal measurable activity, in the phenol red bromination assay, was between about 5 and 9 days for all of the organisms except those in the Botrytis genus.

EXAMPLE VII

Selection of dematiaceous hyphomycetes which produce moderate activity levels of chloroperoxidase Approximately 21 of the 112 ot different species or strains of dematiaceous hyphomycete which were tested were found, in the phenol red assay, to produce an assay optical density, after of 1-24 hours of incubation at optimal temperature, of between 0.5 and 1.2. These organisms were classed as moderate activity level producers. Table IX below lists representative organisms in this group of moderate chloroperoxidase producers, along with the depository numbers and the dematiaceous hyphomycete group classification.

TABLE IX

| GENUS/SPECIE | CMCC # | OTHER # | NRRL # | GROUP |
|---|---|---|---|---|
| Bispora betulina | 0245 | | 15140 | 4 |
| Cladosporium sp. | 0812 | ATCC 20251 | | 4 |
| Cladosporium sp. | 1294 | | 15195 | 4 |
| Stemphylium macrosporidium | 1282 | ATCC 20090 | | 4 |
| Wardomyces anomalus | 0363 | | 15144 | 4 |
| Alternaria sp. | 1287 | | 15193 | 5 |
| Dendryphiella salina | 1282 | CBS 141.60 | | 5 |
| Dendryphion nanum | 1263 | CBS 263.7 | | 5 |
| Ulocladium chartarum | 1289 | | 15149 | 5 |

The growth conditions employed for maximizing chloroperoxidase activity in each of the above-listed fungal organisms is shown below in Table X.

TABLE X

| GENUS/SPECIES | CMCC # | AGAR | GERM. | FERM. | TEMP. | pH | DAY |
|---|---|---|---|---|---|---|---|
| B. betulina | 0245 | V-8 | FA | FA | 19 | 6.86 | 7 |
| Cladosporium sp. | 0812 | V-8 | CF | F4 | 19 | 8.44 | 8 |
| Cladosporium sp. | 1294 | V-8 | F4 | F4 | 19 | 7.97 | 6 |
| S. macrosporidium | 1285 | V-8 | FA | FA | 19 | 7.02 | 8 |
| W. anomalus | 0363 | V-8 | FA | FA | 34 | 7.88 | 9 |
| Alternaria sp. | 1287 | V-8 | F4 | F4 | 25 | 8.01 | 6 |
| D. salina | 1282 | V-8 | FA | CF | 25 | 7.68 | 7 |
| D. nanum | 1263 | V-8 | F4 | CF | 25 | 7.88 | 9 |
| U. chartarum | 1289 | V-8 | FA | FA | 25 | 7.86 | 7 |

EXAMPLE VIII

Preparation of chloroperoxidase from C. inaequalis

C. inaequalis, NRRL #15147, was grown under optimal-growth conditions, as described in Examples I–IV. Following fermentation, the contents of the fermentation flask were disrupted by sonication, and filterred through Whatman #1 filter paper at room temperature. Solid ammonium sulfate was added to the filtrate to produce a 40% saturated ammonium sulfate solution at room temperature. The filtrate-ammonium sulfate mixture was incubated at room temperature for about a half hour, then centrifuged at 10,000 rpm for 90 min. at 4° C., and the precipitate discarded. Additional ammonium sulfate was added to the supernatant to produce at 55% saturated ammonium sulfate solution. The resulting mixture was incubated at room temperature for one-half hour, then centrifuged as described above. The supernatant was discarded and the precipitate (containing the chloroperoxidase) was resuspended in a buffer solution of citrate (100 mM) and ammonium sulfate (500 mM) at pH 5.5. This procedure resulted in a several fold concentration of the chloroperoxidase enzyme, whose activity was measured as 16.28 monochlorodimedon units/mg, as defined in the above Hager reference.

Partially purified chloroperoxidase enzyme fractions were also obtained from Drechslera sp. NRRL #15146 and from Ulocladium sp. NRRL #15200 by substantially identical enzyme purification procedures.

EXAMPLE IX

Chlorination of allyl chloride by C. inaequalis haloperoxidase

A reaction medium containing 30 mM KCl, 0.3 M $KPO_4$ buffer, pH 5.5, 10 mM $H_2O_2$ and 20 mM allyl chloride (Aldrich Chemical Company, Milwaukee, WI) was prepared. To 10 ml of the reaction mixture in a 25 ml Pyrex flask was added the chloroperoxidase isolated as above from C. inaequalis, NRRL #15147, corresponding to 16 monochlorodimedon units. The reaction was carried out for 5 hours at room temperature.

The reaction products were identified by gas chromatography-mass spectrometry (GCMS). Ten (10) microliters of the reaction mixture were injected into a Finnigan 4021 GCMS equipped with a 6 foot $\times$ 4 mm coiled, glass column packed with Texax-GC (80/100 mesh). Flow rate through the column was set at 30 ml/minute of helium. The column temperature was 190° C. (isothermal), and the injection and separator temperatures were both 240° C. The mass spectrometer was operated at 70 eV electron impact ionizaton.

The products were quantitated by gas chromatography (GC) using flame ionization detection (FID). Five (5) microliters of the reaction mixture was injected into a Variam 3700 GC, equipped with a 6 foot $\times$ 4 mm coiled glass column packed with Tenax-GC (80/mesh). Flow rate through the column was set at 40 ml/minute of helium. The temperature conditions were identical to those above.

Of the two products observed by GCMS, one had a GC retention time of 5 minutes and showed the mass spectrum diagnostic for 1,3-dichloro-2-propanol, as confirmed by the GC retention time and mass spectrum of an authentic sample of 1,3-dichloro-2-propanol (purchased from Aldrich Chemical Company).

The other product had a GC retention time of 6 minutes and showed the mass spectrum diagnostic for 2,3-dichloro-1-propanol, as confirmed by the GC retention time and mass spectrum of an authentic sample of 2,3-dichloro-1-propanol (purchased from Aldrich Chemical Company). Quantitation of the products showed that 1,3-dichloro-2-propanol and 2,3-dichloro-1-propanol products constituted about 54% and 46%, respectively, of the total yield (about 4.1 mg). Both products were converted to epichlorohydrin by addition of lime to the aqueous reaction mixture until the pH was greater than 10. Identity of epichlorohydrin was confirmed by gas chromatography-mass spectrometry comparison with an authentic epichlorohydrin sample (purchased from Aldrich Chemical Company). Similar results were obtained at pH 5.0 and 6.0.

EXAMPLE X

Chlorination of allyl alcohol by C. inaequalis haloperoxidase in the presence of sea water A reaction medium containing seawater (collected off the Monterey, California coast) at a final chloride concentration of 400 mM, 0.3 M $KPO_4$, pH 5.0, 10mM $H_2O_2$ and 24 mM allyl alcohol (Aldrich Chemical Company) was prepared. Chlorination of substrate by C. inaequalis, NRRL #15147, chloroperoxidase was performed under the conditions described in Example IX.

Three products were detected. Of these, one product has a GC retention time of 6 minutes and showed the mass spectrum diagnostic for 2,3-dichloro-1-propanol, identical to that of an authentic sample of 2,3-dichloro-1-propanol. Two other products had GC retention times of 7 and 8 minutes, and showed the mass spectra diagnostic for chloropropanediols. The product having a 7 minute retention time was identified as 1-chloro-2,3-propanediol by mass spectrographic analysis. The product having an 8 minute retention time was identified as 2-chloro-1,3-propanediol. The relative percentages of 2,3-dichloro-1-propanol 1-chloro-2,3-propanediol and 2-chloro-1,3-propanediol produced in the reaction were 82%, 10% and 8%, respectively.

As a further confirmation of the identities of the products, 2,3-dichloro-1-propanol was converted to epichlorohydrin by addition of lime to the aqueous reaction mixture until the pH was greater than 10. Identity of epichlorohydrin was confirmed by gas chromatography-mass spectrometry comparison with an authentic sample. The two chloro-propanediols were converted to glycidol by addition of lime to the aqueous reaction mixture until the pH was greater than 10. Identity of glycidol was confirmed by gas chromatography-mass spectrometry comparison with an authentic sample (purchased from Aldrich Chemical Company).

EXAMPLE XI

A reaction medium containing seawater was prepared as in Example X, except that KBr was added to a final concentration of 100 mM. Upon reaction with the C. inaequalis chloroperoxidase, under conditions like those in Example X, the following products were obtained from allyl alcohol: 3-chloro-2-bromo-1-propanol; 3-bromo-2-chloro-1-propanol; 2,3-dichloro-1-propanol; 2,3-dibromo-1-propanediol; and chloro and bromo propanediols.

EXAMPLE XII

Reactions similar to those described in Examples X and XI were carried out in unbuffered seawater (pH 7.49), and in unbuffered seawater spiked with 100 mM KBr. The products obtained were the same of those obtained in Examples X and XI, respectively.

EXAMPLE XIII

Oxidation of iodide ions to molecular iodine

A reaction medium containing potassium iodide at a final iodide concentration of about 80 mM, 0.1M $KPO_4$ buffer, pH 7.0, and $H_2O_2$ at a final concentration of about 8 mM was prepared. To 5 ml of the reaction mixture in a 25 ml Pyrex flask was added haloperoxidase enzyme isolated as above from C. inaequalis, NRRL #15147, corresponding to 16 monochlorodimedon units. The reaction was carried out for 1 hour at room temperature and pressure, and after which 10 ml chloroform was added to the reaction flask. After shaking, the violet coloration of the choroform layer due to dissolved iodine was measured spectrophotometrically at 510 nm. Iodine standards were prepared by dissolving known amounts of iodine (Baker Chemical Company, 99.9% pure) in chloroform. The amount of iodine produced in the reaction was about 8.2 mg.

Product identity was confirmed by injection 10 microliters of the reaction mixture into a Finnigan Model 4021 gas chromatograph/mass spectrometer/data system, equipped with a 6 foot by ¼ inch coiled, glass column, packed with Tenax-GC (60/80 mesh). Carrier gas (helium) flow rate was set at 25 ml/minute. The column temperature was programmed from 100° C. to 250° C. at a rate of 10° C./minute. The mass spectrometer was set on electron impact ionization mode, 70 eV. Iodine eluted from the column near 200° C., and had a characteristic mass spectrum: 2 single peaks of high abundance, m/e 127 and m/e 254.

From the foregoing, it can be appreciated how various objects of the invention are met. The fungal haloperoxidase enzyme can be obtained in large quantities by relatively inexpensive fermentation techniques. The haloperoxidase enzyme can be used in the form of immobilized, undisrupted cells preferably immobilized, or in the form of relatively pure enzyme. Because it has an effective pH range between about pH 4 and 9, the enzyme can be used in a variety of commercial-scale halogenation processes—either one-step or coupled reactions—which are carried out in a neutral or basic pH range. The enzyme can also be used in processes for recovering molecular iodine, in reactions performed in the pH 4–9 range.

Another important feature of the present invention is that the enzyme is capable of oxidizing either chloride, bromide or iodide ions in the halogenation reaction which is performed. This feature enhances the versatility of the halogenation method, and as shown in Example X-XII, allows an inexpensive source of chloride ions such as seawater to be used.

While specific examples illustrating the present invention have been described, it will be appreciated that various changes and modifications can be made without departing from the spirit of the invention.

What is claimed is:

1. A method of oxidizxing a halide selected from the group consisting of chloride, bromide, and iodide, at a selected pH between about 4 and 9, said method comprising:
   providing an enzxyme which is derived from a fungus selected from the group consisting of the genera Alternaria, Curvularia, Drechslera, Ulocladium, Dendryphiella, Dendrylphion therefore Dichotomophthora and Embellisia in the enteroblastic tretic group or from a dmeatiaaceous hyphomycete fungus selected from the group consisting of the genera Botrytis, Bispora, Cladosporium, Humicola, Stemplyllium, Wardomyces and Epicoccum in the acroauxic holoblastic group, and which is capable of chlorinating monochlorodimedon in the presence of H2O2 and chloride ions, at pH 7.0, and reacting the halide with the enzyme in the presence of $H_2O_2$ at the selected pH.

2. The method of claim 1, wherein said halide includes chloride.

3. The method of claim 1, wherein the halide includes bromide.

4. The method of claim 1, wherein the halide includes iodide.

5. The method of claim 1, wherein said reacting is performed at a selected pH between about 6 and 8.

6. The method of claim 1, wherein said reacting is performed at a selected pH between about 5 and 6.

7. The method of claim 1, wherein the fungus is selected from one of the following organisms:

| GENUS/SPECIE | CMCC # | OTHER # | NRRL # | GROUP |
|---|---|---|---|---|
| Alternaria alternata | 1286 | | 15150 | 5 |
| Alternaria alternata | 1288 | | 15291 | 5 |
| Alternaria alternata | 0514 | | 15289 | 5 |
| Alternaria sp. | 1287 | | 15193 | 5 |
| Curvularia cymbopogonis | 0850 | ATCC 38580 | | 5 |
| Curvularia inaequalis | 1262 | ATCC 14992 | | 5 |
| Curvularia inaequalis | 0755 | | 15147 | 5 |
| Curvularia tuberculata | 0842 | ATCC 15058 | | 5 |
| Curvularia verruciformis | 0844 | QM 8326 | | 5 |
| Curvularia lunata | 0843 | ATCC 12017 | | 5 |
| Curvularia lunata | 1296 | | 15293 | 5 |
| Curvularia lunata | 1297 | | 15196 | 5 |
| Dichotomophthora portulacae | 1288 | CBS 239.48 | | 5 |
| Drechslera halodes | 1299 | | 15151 | 5 |
| Drechslera sp. | 0834 | | 15290 | 5 |
| Drechslera sp. | 0835 | | 15146 | 5 |
| Drechslera sp. | 1302 | | 15294 | 5 |
| Drechslera sp. | 1290 | | 15197 | 5 |
| Ulocladium sp. | 0282 | | 15200 | 5 |
| Ulocladium sp. | 1291 | | 15201 | 5 |
| Ulocladium sp. | 1292 | | 15102 | 5 |
| Ulocladium sp. | 1300 | | 15103 | 5 |
| Ulocladium sp. | 1301 | | 15104 | 5 |
| Botrytis cinerea | 0311 | | 15327 | 4 |
| Botrytis sp. | 0253 | | 15326 | 4 |
| Botrytis sp. | 0256 | | 15309 | 4 |
| Botrytis sp. | 1293 | | 15292 | 4 |
| Dendryphiella salina | 1282 | CBS 141.60 | | 5 |
| Dendryphion nanum | 1263 | CBS 263.70 | | 5 |
| Ulocladium chartarum | 1289 | | 15149 | 5 |
| Bispora betulina | 0245 | | 15140 | 4 |
| Cladosporium sp. | 0812 | ATCC 20251 | | 4 |
| Cladosporium sp. | 1294 | | 15195 | 4 |
| Humicola fuscoatra | 0397 | | 15198 | 4 |
| Stemphylium macrosporidium | 1285 | ATCC 20090 | | 4 |
| Wardomyces anomalus | 0363 | | 15144 | 4 |
| Embellisia allii | 1305 | | 15148 | 5 |

8. The method of claim 7, wherein the fungus is selected from one of the following organisms.

| GENUS/SPECIE | CMCC # | OTHER # | NRRL # | GROUP |
|---|---|---|---|---|
| Alternaria alternata | 1286 | | 15150 | 5 |
| Alternaria alternata | 1288 | | 15291 | 5 |
| Alternaria alternata | 0514 | | 15289 | 5 |
| Curvularia cymbopogonis | 0850 | ATCC 38580 | | 5 |
| Curvularia inaequalis | 1262 | ATCC 14992 | | 5 |
| Curvularia inaequalis | 0755 | | 15147 | 5 |
| Curvularia lunata | 0843 | ATCC 12017 | | 5 |
| Curvularia tuberculata | 0842 | ATCC 15058 | | 5 |
| Curvularia verruciformis | 0844 | QM 8326 | | 5 |
| Curvularia lunata | 1296 | | 15293 | 5 |
| Curvularia lunata | 1297 | | 15196 | 5 |
| Dichotomophthora portulacae | 1288 | CBS 239.48 | | 5 |
| Drechslera halodes | 1299 | | 15151 | 5 |
| Drechslera sp. | 0834 | | 15290 | 5 |
| Drechslera sp. | 0835 | | 15146 | 5 |
| Drechslera sp. | 1302 | | 15294 | 5 |
| Drechslera sp. | 1290 | | 15197 | 5 |

-continued

| GENUS/SPECIE | CMCC # | OTHER # | NRRL # | GROUP |
|---|---|---|---|---|
| Ulocladium sp. | 0282 | | 15200 | 5 |
| Ulocladium sp. | 1291 | | 15201 | 5 |
| Ulocladium sp. | 1292 | | 15102 | 5 |
| Ulocladium sp. | 1300 | | 15103 | 5 |
| Ulocladium sp. | 1301 | | 15104 | 5 |
| Botrytis cinerea | 0311 | | 15327 | 4 |
| Botrytis sp. | 0253 | | 15326 | 4 |
| Botrytis sp. | 0256 | | 15309 | 4 |
| Botrytis sp. | 1293 | | 15292 | 4 |
| Epicoccum nigrum | 1268 | | 15143 | 4 |
| Embellisia allii | 1305 | | 15148 | 5 |

9. The method of claim 8, wherein the fungus includes C. inaequalis, NRRL #15147.

10. The method of claim 8, wherein the fungus includes Drechslera sp. NRRL #15146.

11. The method of claim 1, wherein said providing includes isolating from a soluble fraction of fungal growth material, an enzyme which precipitates between about 40% and 55% saturated ammonium sulfate.

12. The method of claim 1, wherein the enzxyme is provided in undisrupted cells of the selected fungus, and said reacting includes immobilizing the undisrupted cells on a solid support and reacting the immobilized cells with the compound under the selected reaction conditions.

13. The method of claim 1 further including before said reacting step, providing a compound to be halogenated, selected from one of the group consistging of alkenes, alkynes, cyclopropanes, beta-keto acids, cyclic beta-diketone and aromatic ring compounds.

14. The method of claim 13, wherein the compound to be halogenated includes an alkene.

15. A method of oxidizing iodide ions to molecular iodine, at a selected pH between about 4.0 and 9.0, in the presence of $H_2O_2$, said method comprising:

producing an enyzme which is derived from a dematiaceous hyphomycetes fungus selected from the group consisting of the genera Alternaria, Curvularia, Drechslera, Ulocladium, Dendryphiella, Dendryphion and Dichotomophthora in the enteroblastic tretic group or from a dematiaceous hyphomycete fungus selected from the group consisting of the genera Botryts, Bispora, Cladosporium, Humicola, Stemphyllium, Wardomyces and Epicoccum in the acroauxtic holoblastic group, and which is capable of chlorinating monochlorodimedon in the presence of hydrogen peroxide and chlorine ions, at pH 7.0, and reacting the enzyme with an iodide salt in the presence of $H_2O_2$, at the selected pH.

* * * * *

UNITED STATES PATENT AND TRADEMARK OFFICE
CERTIFICATE OF CORRECTION

PATENT NO. : 4,707,447

DATED : November 17, 1987

INVENTOR(S) : Jennie C. Hunter, Angela Belt, Lynn S. Sotos, Michelle E. Fonda

Page 1 of 3

It is certified that error appears in the above-identified patent and that said Letters Patent is hereby corrected as shown below:

Column 8, Line 5, change "Growlh" to --Growth--
Column 8, Line 61, change "(0.2g)" to --(2.0g)--
Column 8, Line 66, change "0.02%" to --0.2%--
Column 9, Line 1, change "(0.2g)" to --(2.0g)--
Column 11, Line 21, change "organism" to --organisms--
Column 12, Line 26, change "NRR1" to --NRRL--
Column 12, Line 31, change "alternata" to --sp--
Column 12, Line 47, change "15102" to --15202--
Column 12, Line 48, change "15103" to --15203--
Column 12, Line 49, change "15104" to --15204--
Column 13, Line 59, delete "ot"
Replace Columns 13 and 14 with the attached Columns 13 and 14
Column 17, Line 47, change "oxidizxing" to --oxidizing--
Column 17, Line 51, change "enzxyme" to --enzyme--
Column 17, Line 56, change "dmeatiaceous" to --dematiaceous--
Column 17, Line 59, change "Stemplyllium" to --Stemplylium--
Column 18, Line 14, change "alternata" to --sp--
Column 18, Line 32, change "15102" to --15202--
Column 18, Line 33, change "15103" to --15203--
Column 18, Line 34, change "15104" to --15204--
Column 18, Line 54, change "alternata" to --sp--
Column 19, Line 7, change "15102" to --15202--
Column 19, Line 8, change "15103" to --15203--
Column 19, Line 9, change "15104" to --15204--
Column 19, Line 25, change "enzxyme" to --enzyme--
Column 20, Line 5, change "consistging" to --consisting--

UNITED STATES PATENT AND TRADEMARK OFFICE
CERTIFICATE OF CORRECTION

PATENT NO. : 4,707,447

DATED : November 17, 1987

INVENTOR(S) : Jennie C. Hunter et al.

It is certified that error appears in the above-identified patent and that said Letters Patent is hereby corrected as shown below:

Column 20, Line 21, change "Stemphyllium" to -- Stemphylium --.

Signed and Sealed this

Eighth Day of November, 1988

Attest:

DONALD J. QUIGG

*Attesting Officer*  *Commissioner of Patents and Trademarks* mum activity level was observed. The particular fungal agar, germination broth, fermentation broth, fermentation temperature, and fermentation period for each of the organisms listed in Table VII are shown in Table VIII.

TABLE VIII

| ORGANISM | CMCC # | AGAR | GERM | FERM | TEMP | pH | DAY |
|---|---|---|---|---|---|---|---|
| A. alternata | 1286 | FA | CF | CF | 34 | 7.60 | 6 |
| A. alternata | 1288 | FA | FA | CF | 34 | 7.65 | 8 |
| A. alternata | 0914 | FA | FA | F4 | 25 | 8.12 | 7 |
| C. cymbopogonis | 0850 | H₂O | F4 | F4 | 19 | 8.40 | 6-8 |
| C. inaequalis | 1262 | H₂O | FA | F4 | 25 | 8.52 | 7 |
| C. inaequalis | 0755 | FA/H₂O | FA | CF | 25 | 8.26 | 7 |
| C. lunata | 0843 | H₂O | F4 | F4 | 25 | 8.35 | 8 |
| C. tuberculata | 0842 | H₂O | F4 | F4 | 34 | 8.12 | 9 |
| C. verruciformis | 0844 | H₂O | F4 | F4 | 34 | 8.43 | 8 |
| C. lunata | 1296 | FA | F4 | F4 | 25 | 8.68 | 6 |
| C. lunata | 1297 | H₂O | F4 | F4 | 25 | 8.37 | 8 |
| D. portulacae | 1223 | H₂O | F4 | F4 | 25 | 7.96 | 6 |
| D. halodes | 1299 | H₂O | FA | FA | 25 | 8.33 | 7 |
| Drechslera sp. | 0834 | V8 | F4 | F4 | 25 | 6.50 | 9 |
| Drechslera sp. | 0835 | V8 | FA | CF | 25 | 8.36 | 8 |
| Drechslera sp. | 1302 | FA | F4 | F4 | 25 | 8.49 | 6 |
| Drechslera sp. | 1290 | V8 | CF | F4 | 34 | 7.60 | 6 |
| Ulocladium sp. | 0832 | V8 | FA | FA | 19 | 8.40 | 7 |
| Ulocladium sp. | 1291 | V8 | FA | FA | 34 | 7.72 | 7 |
| Ulocladium sp. | 1292 | V8 | FA | CF | 25 | 7.80 | 8 |
| Ulocladium sp. | 1300 | V8 | FA | CF | 34 | 7.42 | 6-7 |
| Ulocladium sp. | 1301 | V8 | FA | CF | 25 | 7.79 | 7 |
| B. cinerea | 0311 | PDA | F4 | F4 | 25 | 5.30 | 13 |
| Botrytis sp. | 0253 | PDA | F4 | F4 | 25 | 7.00 | 15 |
| Botrytis sp. | 0256 | PDA | F4 | F4 | 25 | 7.30 | 12 |
| Botrytis sp. | 1293 | FA | F4 | F4 | 25 | 8.60 | 8 |

Also listed in Table VIII, in the second column from the right, is the pH of the fermentation broth, measured at the end of the fermentation period. It can be appreciated from the table that all but one (*B. cinerea*) of the high-activity producers were characterized by a fermentation broth pH of between about 6.5 and 8.5. Further, the length of fermentation needed to produce optimal measurable activity, in the phenol red bromination assay, was between about 5 and 9 days for all of the organisms except those in the Botrytis genus.

EXAMPLE VII

Selection of dematiaceous hyphomycetes which produce moderate activity levels of chloroperoxidase Approximately 21 of the 112 or different species or strains of dematiaceous hyphomycete which were tested were found, in the phenol red assay, to produce an assay optical density, after of 1-24 hours of incubation at optimal temperature, of between 0.5 and 1.2. These organisms were classed as moderate activity level producers. Table IX below lists representative organisms in this group of moderate chloroperoxidase producers, along with the depository numbers and the dematiaceous hyphomycete group classification.

TABLE IX

| GENUS/SPECIE | CMCC # | OTHER # | NRRL # | GROUP |
|---|---|---|---|---|
| Bispora betulina | 0245 | — | 15140 | 4 |
| Cladosporium sp. | 0812 | ATCC 20251 | | 4 |
| Cladosporium sp. | 1294 | | 15195 | 4 |
| Stemphylium macrosporidium | 1282 | ATCC 20090 | | 4 |
| Wardomyces anomalus | 0363 | | 15144 | 4 |
| Alternaria sp. | 1287 | | 15193 | 5 |
| Dendryphiella salina | 1282 | CBS 141.60 | | 5 |
| Dendryphion nanum | 1263 | CBS 263.7 | | 5 |
| Ulocladium chartarum | 1289 | | 15149 | 5 |

The growth conditions employed for maximizing chloroperoxidase activity in each of the above-listed fungal organisms is shown below in Table X.

TABLE X

| GENUS/SPECIES | CMCC # | AGAR | GERM | FERM | TEMP | pH | DAY |
|---|---|---|---|---|---|---|---|
| B. betulina | 0245 | V-8 | FA | FA | 19 | 6.86 | 7 |
| Cladosporium sp. | 0812 | V-8 | CF | F4 | 19 | 8.44 | 8 |
| Cladosporium sp. | 1294 | V-8 | F4 | F4 | 19 | 7.97 | 6 |
| S. macrosporidium | 1285 | V-8 | FA | FA | 19 | 7.02 | 8 |
| W. anomalus | 0363 | V-8 | FA | FA | 34 | 7.88 | 9 |
| Alternaria sp. | 1287 | V-8 | F4 | F4 | 25 | 8.01 | 6 |
| D. salina | 1282 | V-8 | FA | CF | 25 | 7.68 | 7 |
| D. nanum | 1263 | V-8 | F4 | CF | 25 | 7.88 | 9 |
| U. chartarum | 1289 | V-8 | FA | FA | 25 | 7.86 | 7 |

EXAMPLE VIII

Preparation of chloroperoxidase from *C. inaequalis*

*C. inaequalis*, NRRL #15147, was grown under optimal-growth conditions, as described in Examples I-IV. Following fermentation, the contents of the fermentation flask were disrupted by sonication, and filtered through Whatman #1 filter paper at room temperature. Solid ammonium sulfate was added to the filtrate to produce a 40% saturated ammonium sulfate solution at room temperature. The filtrate-ammonium sulfate mixture was incubated at room temperature for about a half hour, then centrifuged at 10,000 rpm for 90 min. at 4° C., and the precipitate discarded. Additional ammo-

UNITED STATES PATENT AND TRADEMARK OFFICE
CERTIFICATE OF CORRECTION

PATENT NO. : 4,707,447

DATED : November 17, 1987

INVENTOR(S) : Jennie C. Hunter, Angela Belt, Lynn S. Sotos, Michelle E. Fonda

It is certified that error appears in the above-identified patent and that said Letters Patent is hereby corrected as shown below:

Column 18, Line 45, Claim 7, delete "Embellisia allii    1305    15148    5".

Column 19, Line 14, Claim 8, delete "Embellisia allii    1305    15148    5".

Signed and Sealed this

Eleventh Day of June, 1991

Attest:

HARRY F. MANBECK, JR.

Attesting Officer

Commissioner of Patents and Trademarks